(12) United States Patent
Smith et al.

(10) Patent No.: US 11,819,692 B2
(45) Date of Patent: Nov. 21, 2023

(54) COCHLEAR IMPLANTS HAVING DETACHABLE FIXATION ELEMENTS AND ASSOCIATED SYSTEMS AND METHODS

(71) Applicant: ADVANCED BIONICS AG, Staefa (CH)

(72) Inventors: James George Elcoate Smith, Valencia, CA (US); Matt V. Krywcun, Saugus, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 17/964,984

(22) Filed: Oct. 13, 2022

(65) Prior Publication Data

US 2023/0035478 A1 Feb. 2, 2023

Related U.S. Application Data

(62) Division of application No. 16/038,357, filed on Jul. 18, 2018, now Pat. No. 11,497,910.

(60) Provisional application No. 62/535,149, filed on Jul. 20, 2017.

(51) Int. Cl.
| | |
|---|---|
| *A61N 1/375* | (2006.01) |
| *A61N 1/36* | (2006.01) |
| *A61N 1/05* | (2006.01) |
| *A61N 1/372* | (2006.01) |

(52) U.S. Cl.
CPC ....... *A61N 1/36038* (2017.08); *A61N 1/0541* (2013.01); *A61N 1/37217* (2013.01); *A61N 1/37229* (2013.01); *A61N 1/37518* (2017.08)

(58) Field of Classification Search
None
See application file for complete search history.

(56) References Cited

U.S. PATENT DOCUMENTS

| | | | |
|---|---|---|---|
| 7,937,156 B2 * | 5/2011 | Gibson | A61N 1/375 607/57 |
| 7,974,700 B1 * | 7/2011 | Gibson | A61N 1/36046 607/57 |
| 8,230,604 B1 * | 7/2012 | Corey | B25G 3/08 30/301 |
| 8,774,929 B2 | 7/2014 | Gibson | |
| 9,731,128 B2 * | 8/2017 | Leigh | A61N 1/37223 |
| 2006/0116743 A1 | 6/2006 | Gibson et al. | |
| 2009/0099658 A1 | 4/2009 | Dalton et al. | |
| 2010/0049318 A1 * | 2/2010 | Jolly | A61N 1/36038 623/10 |
| 2013/0225912 A1 | 8/2013 | Leigh | |
| 2014/0309747 A1 * | 10/2014 | Taylor | A61B 17/846 623/23.39 |
| 2015/0151026 A1 | 6/2015 | Gibson | |
| 2015/0246234 A1 | 9/2015 | Hazard et al. | |
| 2016/0001076 A1 | 1/2016 | Nielsen | |
| 2016/0199638 A1 * | 7/2016 | Xu | A61N 1/36036 607/137 |

* cited by examiner

*Primary Examiner* — Erica S Lee
(74) *Attorney, Agent, or Firm* — Henricks Slavin LLP

(57) ABSTRACT

A cochlear implant includes a cochlear lead, a housing, an antenna, a stimulation processor operably connected to the antenna and to the cochlear lead, a first fixation element, a second fixation element with a different configuration than the first fixation element, and a connector configured to simultaneously connect the first and second fixation elements to the housing in such a manner that the first and second fixation elements are independently detachable from the housing.

14 Claims, 12 Drawing Sheets

COCHLEAR IMPLANTS HAVING DETACHABLE FIXATION ELEMENTS AND ASSOCIATED SYSTEMS AND METHODS

CROSS-REFERENCE TO RELATED APPLICATIONS

This application is a divisional of U.S. application Ser. No. 16/038,357, filed Jul. 18, 2018, now U.S. Pat. No. 11,497,910, which claims the benefit of U.S. Provisional Application No. 62/535,149, filed Jul. 20, 2017, which is incorporated herein by reference.

BACKGROUND

1. Field

The present disclosure relates generally to the implantable portion of implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Advanced Bionics™ Harmony™ BTE sound processor, the Advanced Bionics™ Naida™ BTE sound processor and the Advanced Bionics™ Neptune™ body worn sound processor.

As alluded to above, some ICS systems include an implantable cochlear stimulator (or "cochlear implant"), a sound processor unit (e.g., a body worn processor or behind-the-ear processor), and a microphone that is part of, or is in communication with, the sound processor unit. The cochlear implant communicates with the sound processor unit and, some ICS systems include a headpiece that is in communication with both the sound processor unit and the cochlear implant. The headpiece communicates with the cochlear implant by way of a transmitter (e.g., an antenna) on the headpiece and a receiver (e.g., an antenna) on the implant. Optimum communication is achieved when the transmitter and the receiver are aligned with one another. To that end, the headpiece and the cochlear implant may include respective positioning magnets that are attracted to one another, and that maintain the position of the headpiece transmitter over the implant receiver. The implant magnet may, for example, be located within a pocket in the cochlear implant housing.

Various techniques have been employed to prevent movement of cochlear implants after they have been surgically implanted. Examples of such movement prevention techniques (or "fixation techniques") include forming a tight pocket for the cochlear implant in the periosteum, drilling a recess (or "bone bed") into the skull at the desired location in the shape of some or all of the cochlear implant housing, attaching bone anchors (e.g., bone screws) to the skull and using the bone anchors to anchor sutures that extend over the cochlear implant, and attaching bone anchors (e.g., bone screws) to the skull after passing the anchors through one or more portions of the cochlear implant. Another technique involves the use of small projections that extend from the cochlear implant housing and osseointegrate with the skull over time. Each cochlear implant surgeon has their own preference and surgeons tend to employ one of these techniques to the exclusion of the others. As a result, cochlear implant manufactures who intend to accommodate the various fixation preferences must provide more than one version of each model of cochlear implant. The present inventor has determined that conventional methods of accommodating surgical preferences are susceptible to improvement and, in particular, that it would be desirable to provide a cochlear implant that surgeons may easily adapt to their preferred fixation techniques.

SUMMARY

A cochlear implant includes a cochlear lead, a housing, an antenna, a stimulation processor operably connected to the antenna and to the cochlear lead, a first fixation element, a second fixation element with a different configuration than the first fixation element, and a connector configured to simultaneously connect the first and second fixation elements to the housing in such a manner that the first and second fixation elements are independently detachable from the housing. The present inventions also include systems with such a cochlear implant in combination with a headpiece.

A kit includes a cochlear implant, a first tool and a second tool. The cochlear implant includes a cochlear lead, a housing, an antenna, a stimulation processor operably connected to the antenna and to the cochlear lead, a first fixation element attached to the housing, and a second fixation element attached to the housing and having a different configuration than the first fixation element. The first tool is configured to detach at least the first fixation element from the housing when the cochlear implant and the first tool are pressed against one another. The second tool is configured to detach at least the second fixation element from the housing when the cochlear implant and the second tool are pressed against one another.

A method in accordance with one of the present inventions includes the steps of detaching at least one of the fixation elements from a cochlear implant by cutting through a portion of the cochlear implant, and implanting the cochlear implant into a patient after the at least one of the fixation elements has been detached.

There are a number of advantages associated with such apparatus and methods. For example, the present implants may be provided to surgeons who prefer to use both bone bed fixation and bone anchor fixation (or bone osseointegration fixation), surgeons who prefer either bone bed fixation or anchor fixation (or bone osseointegration fixation), and surgeons who prefer fixation by way of tight pockets and/or sutures. The surgeon will simply remove unwanted fixation elements (if any) at the time of surgery.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

DETAILED DESCRIPTION OF THE EXEMPLARY EMBODIMENTS

Figure 1:
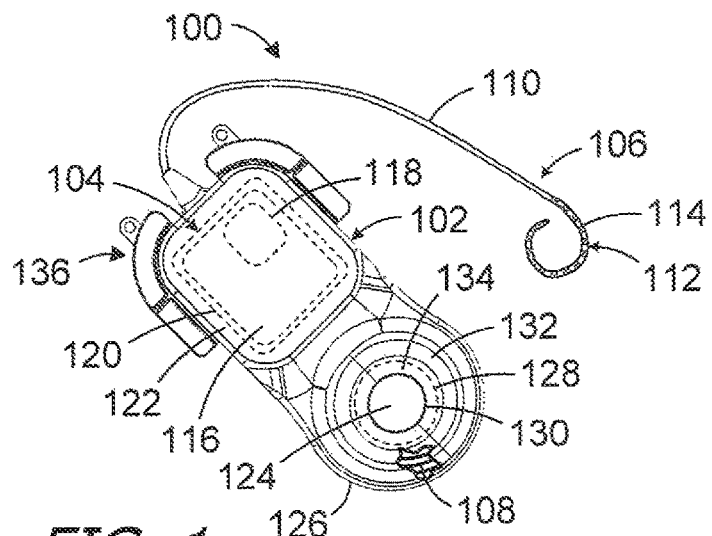
FIG. 1 is a top view of a cochlear implant in accordance with one embodiment of a present invention.
Figure 2:
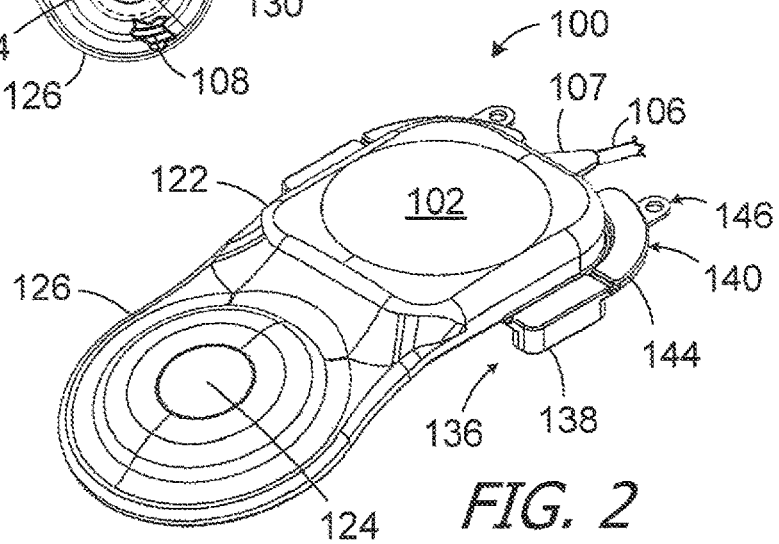
FIG. 2 is a top perspective view of a portion of the cochlear implant illustrated in FIG. 1.

The following is a detailed description of the best presently known modes of carrying out the inventions. This description is not to be taken in a limiting sense, but is made merely for the purpose of illustrating the general principles of the inventions.

One example of a cochlear implant (or "implantable cochlear stimulator") in accordance with at least one of the present inventions is the cochlear implant 100 illustrated in FIGS. 1-9. Referring first to FIGS. 1-4, the exemplary cochlear implant 100 includes a resilient flexible housing 102 formed from a silicone elastomer or other suitable material, a processor assembly 104, a cochlear lead 106, and an antenna 108 that may be used to receive data and power by way of an external antenna that is associated with, for example, a sound processor unit. The cochlear lead 106 may include a flexible body 110, an electrode array 112 at one end of the flexible body 102, and a plurality of wires (not shown) that extend through the flexible body from the electrically conductive contacts 114 (e.g., platinum contacts) in the array 112 to the other end of the flexible body. A strain relief 107 may be provided at the end of the cochlear lead 106. The exemplary antenna 108 is a coil antenna with one or more loops (or "turns"), and three loops are shown in the illustrated embodiment. The exemplary processor assembly 104, which is connected to the electrode array 112 and antenna 108, includes a printed circuit board 116 with a stimulation processor 118 that is located within a hermetically sealed case 120. The stimulation processor 118 converts stimulation data into stimulation signals that stimulate the contacts 114 of the electrode array 112. The hermetically sealed case 120 is located within a processor portion 122 of the housing 102. A positioning magnet 124 is located within an antenna portion 126 of the housing 102. The magnet 124, which is used to maintain the position of a headpiece transmitter over the antenna 108, is centered relative to the antenna 108 and is located within a magnet pocket 128. The magnet 124 can be inserted into, and removed from, the magnet pocket 128 by way of a magnet aperture 130 that extends through the top wall 132 of the housing 102. The magnet 124 is larger than the magnet aperture 130, i.e., the outer diameter of the magnet is greater than the diameter of the magnet aperture, and the portion of the top wall 132 between the aperture 130 and the outer edge of the magnet forms a retainer 134.

The present exemplary cochlear implants may also include a fixation apparatus with a plurality of independently removable fixation elements. For example, some of the fixation elements may be configured for placement in bone beds formed in the skull (e.g., by drilling), while others may be configured for use with bone screws or other bone anchors. In other implements, osseointegration protrusions may be employed in place of the bone anchors. As used herein, an "independently removable" fixation element is a fixation element that can be detached from the cochlear implant without removal of the other fixation elements or destruction of the cochlear implant housing. Thus, the independent removability of the fixation elements provides the surgeon with a number of options, i.e., use all of the fixation elements, use some of the fixation elements, or use none of the fixation elements. As such, the same cochlear implants may be provided to surgeons who prefer to use both bone bed fixation and bone anchor fixation, surgeons who prefer either bone bed fixation or anchor fixation, and surgeons who prefer fixation by way of tight pockets and/or sutures. Alternatively, the same cochlear implants may be provided to surgeons who prefer to use both bone bed fixation and osseointegration fixation, surgeons who prefer either bone bed fixation or osseointegration fixation, and surgeons who prefer fixation by way of tight pockets and/or sutures. In either case, the removal may, for example, be performed quickly at the time of surgery, thereby allowing the cochlear implant and, if provided, detachment apparatus to remain in their sterile packaging until needed.

Figure 3:
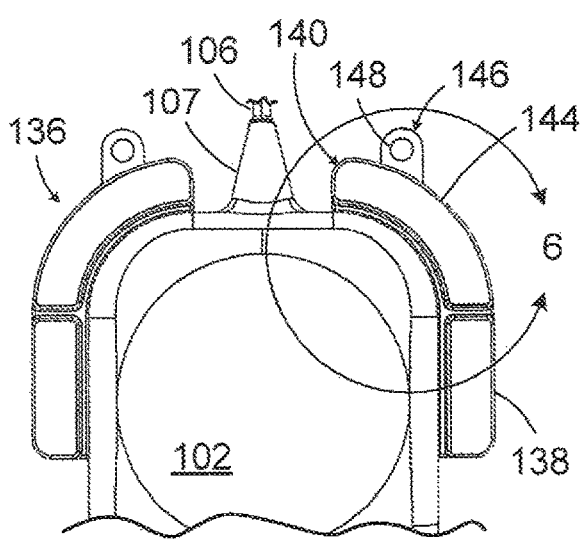
FIG. 3 is a top view of a portion of the cochlear implant illustrated in FIG. 1.
Figure 4:
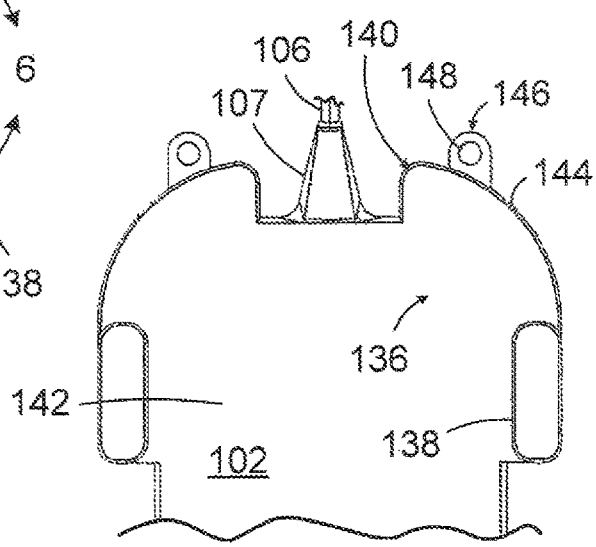
FIG. 4 is a bottom view of a portion of the cochlear implant illustrated in FIG. 1.

Referring more specifically to FIGS. 3 and 4, the exemplary cochlear implant 100 includes a fixation apparatus 136 with fixation elements in the form of a pair of bone bed projections 138 and a pair of anchor receivers 140 that are attached to the housing 102 in a manner that facilitates their removal if desired by the surgeon. The exemplary bone bed projections 138 extend downwardly relative to the bottom surface of the housing bottom wall 142. Accordingly, when the bottom wall 142 is placed against the skull during the implantation procedure, the bone bed projections 138 will extend into the correspondingly sized and shaped indentations (or "bone beds") formed in the skull, thereby fixing the position of the cochlear implant 100. The exemplary anchor receivers 140 include a base 144 and a lug 146, with an aperture 148, which extends outwardly from the base. Bone screws (e.g., standard bone screws and self-drilling bone screws) or other suitable anchors may be inserted through the apertures 148 in the lugs 146 to secure the anchor receiver 140 to bone, thereby fixing the position of the cochlear implant 100.

Figure 5:
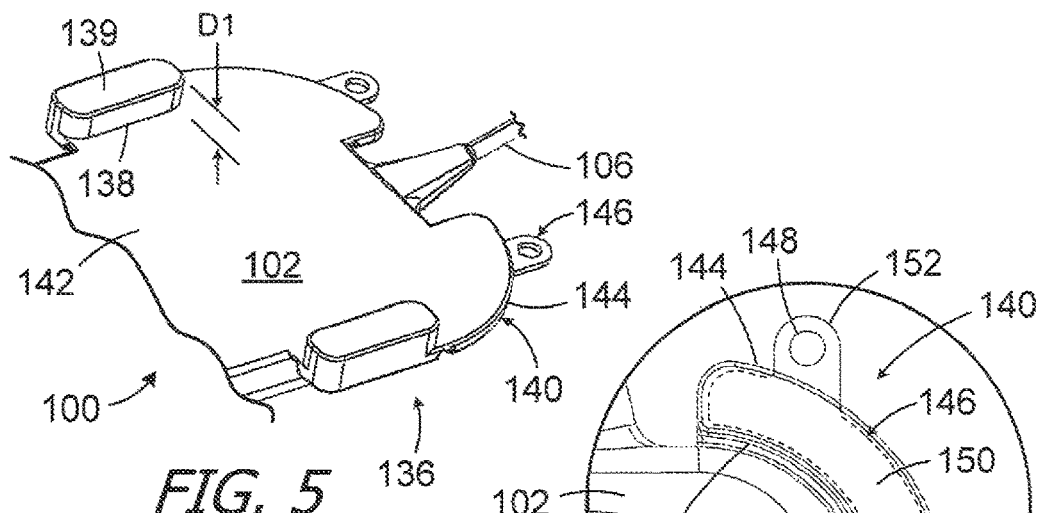
FIG. 5 is a bottom perspective view of a portion of the cochlear implant illustrated in FIG. 1.

Turning to FIG. 5, the bone bed projections 138 may be a rounded rectangular shape (as shown) or any other suitable shape. The distance D1 that the bottom end 139 of the bone bed projections 138 is offset from the housing bottom wall 142 (see also FIG. 9) should be sufficient to prevent post-implantation movement and, in the illustrated implementation, the distance may be about 0.5 mm to about 3.0 mm. It should also be noted that although there are two bone bed projections in the illustrated embodiment, the number of bone bed projections 138 may be increased or decreased.

Figure 6:
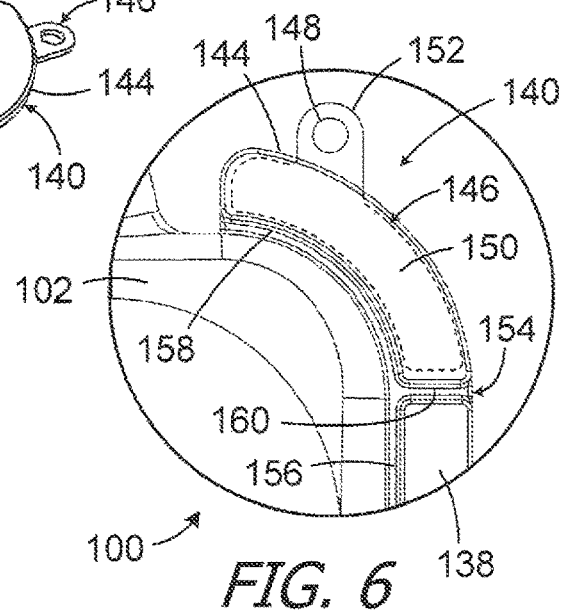
FIG. 6 is an enlarged view of a portion of FIG. 3.
Figure 7:
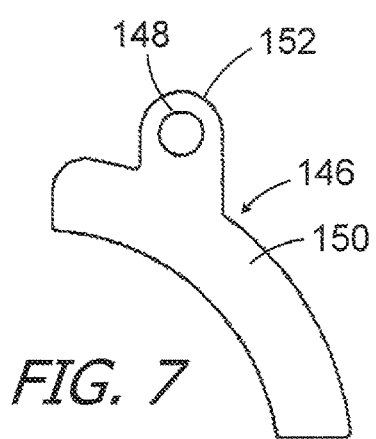
FIG. 7 is a plan view of a portion of the cochlear implant illustrated in FIG. 1.

Referring to FIGS. 6 and 7, the exemplary lugs 146 are partially embedded within the bases 144 of the anchor receivers 140. In particular, the lugs 146 each include an embedded portion 150 that is located within the associated base 144 and a tab 152 that projects outwardly from the base. The apertures 148 are formed in the tabs 152, which are for the most part unembedded (i.e., no surface is covered by the material that forms the base 144). There are a number of advantages associated with anchor receivers having only partially embedded lugs with exposed apertures. For example, the lugs 146 may be partially embedded within the bases 144 by way of a relatively simple insert molding process that is unlikely to result in flashover over the apertures 148. During use, silicone (or other housing material) will not interfere with placement of the anchors through the apertures 148.

In other implementations, the number of anchor receivers may be increased or decreased and/or the number of tabs (and apertures) associated with each anchor receiver may be increased. In still other implementations, the tabs 152 may be omitted and the apertures 148 may be formed in the embedded portions 150 (with corresponding apertures formed in the bases 144). The lugs 146 may also be omitted and, in those instances where a tab 152 is present, the tab may simply be an integral part of the base 144.

Figure 8:
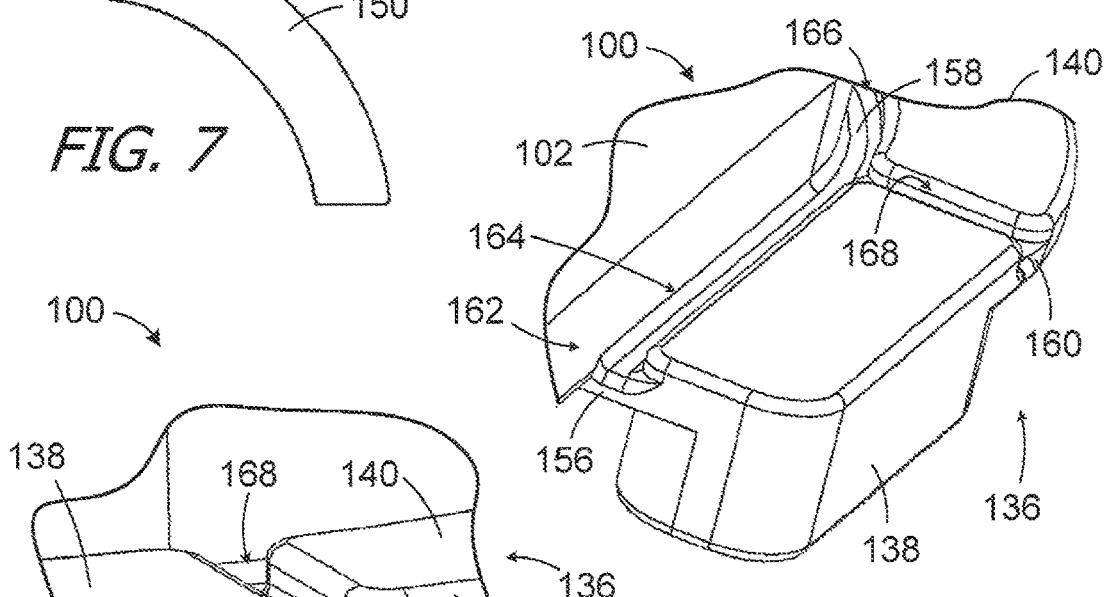
FIG. 8 is a top perspective view of a portion of the cochlear implant illustrated in FIG. 1.
Figure 9:
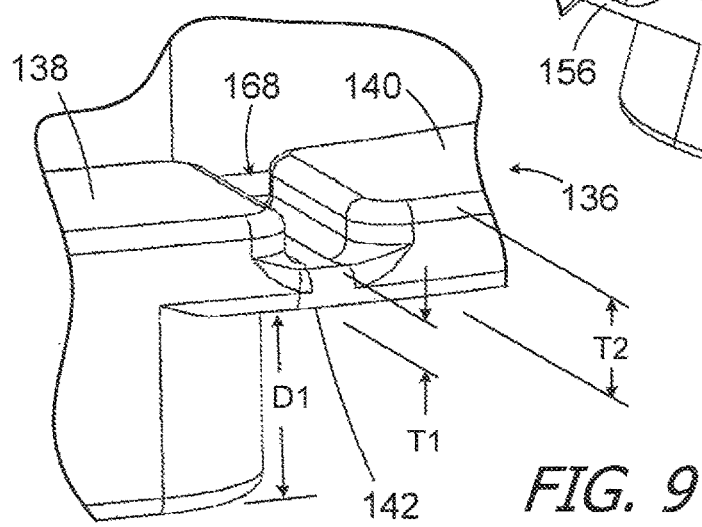
FIG. 9 is a top perspective view of a portion of the cochlear implant illustrated in FIG. 1.

As noted above, the bone bed projections 138 and anchor receivers 140 may be attached to the housing 102 in a manner that facilitates their detachment and removal by the surgeon. In the illustrated implementation, and as can be seen in FIGS. 6, 8 and 9, the exemplary fixation apparatus 136 includes a pair of thin connectors 154 with connector portions 156, 158 and 160. Each connector 154 connects one bone bed projection 138 and one anchor receiver 140 to the housing 102 as well as to one other. The spacing of the bone bed projections 138 and anchor receivers 140 from the housing 102, and from one another, as well as the difference between the thickness T1 of the connectors 154 and thickness T2 of the fixation apparatus 136 (as measured from the bottom surface of the bottom wall 142), results in indentations 162 with indentation portions 164, 166 and 168. The thin connectors 154 facilitate detachment and removal of the bone bed projections 138 and/or the anchor receivers 140 from the housing 102 by providing a relatively thin and easy to cut or otherwise sever connections that are nevertheless strong enough to remain intact post-implantation (when not severed). The indentations 162 facilitate detachment and removal of the bone bed projections 138 and/or the anchor receivers 140 from the housing 102 by providing a guide for the tool that is used to sever the appropriate connector portions 156, 158 and/or 160.

The exemplary fixation apparatus 136 in the illustrated embodiment may be integrally molded with and, but for the lugs 146, formed from the same material as, the housing 102. As a result, but for the lugs 146 (if present), the housing 102, bone bed projections 138 and anchor receivers 140 together define an integrally molded one-piece structure. Suitable materials for the lugs 146 include, but are not limited to, metals such as titanium and stainless steel, biocompatible polymers such as PEEK and liquid crystal polymer.

The manner which the bone bed projections 138 and anchor receivers 140 are attached to housing 102 is not limited to the exemplary thin connectors 154. By way of example, but not limitation, serrations may be added to the connectors 154 so that the bone bed projections 138 and anchor receivers 140 can be detached by tearing, instead of cutting in the manner described below. Alternatively, or in addition, the connectors 154 may be formed from a material that is different than the housing material and that is more susceptible to cutting or tearing than the housing material. For example, the connector material may be a material that weakens when exposed to UV light. Here, the connector portions 156, 158 and 160 may be masked with respective removable pieces of tape. The tape will be removed from the connector portions 156, 158 and/or 160 that are to be severed prior to the exposure to UV light. The thickness of the connector 154 may also be increased to that of the fixation apparatus 136 and, in at least some instances, indicia may be added to visibly identify the locations where detachment of the bone bed projections 138 and anchor receivers 140 should occur.

Figure 9A:
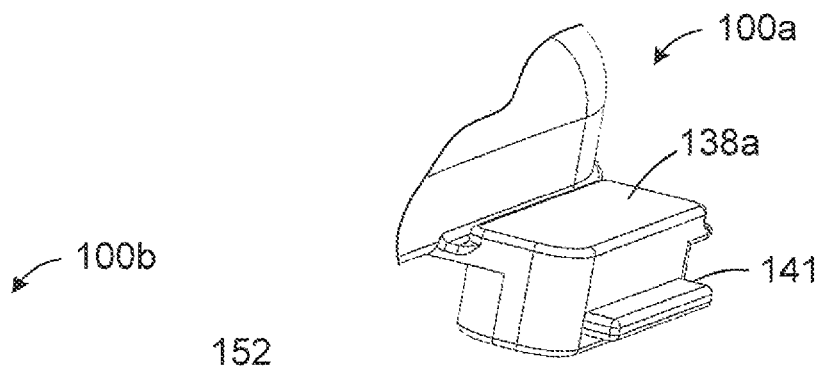
FIG. 9A is a top perspective view of a portion of a cochlear implant in accordance with one embodiment of a present invention.

The present bone bed projections may also be configured for use with bone beds which include an undercut that is located below, and is parallel to, the outer surface of the skull. The exemplary cochlear implant 100a illustrated in FIG. 9A, which is otherwise identical to cochlear implant 100, includes a bone bed projection 138a that is configured for use with a bone bed having such an undercut. In particular, the bone bed projection 138a includes a flexible cantilevered flap 141 that will deflect as the bone bed projection is pressed into the bone bed, and then return to its unstressed shape when it reaches the undercut.

Figure 9B:
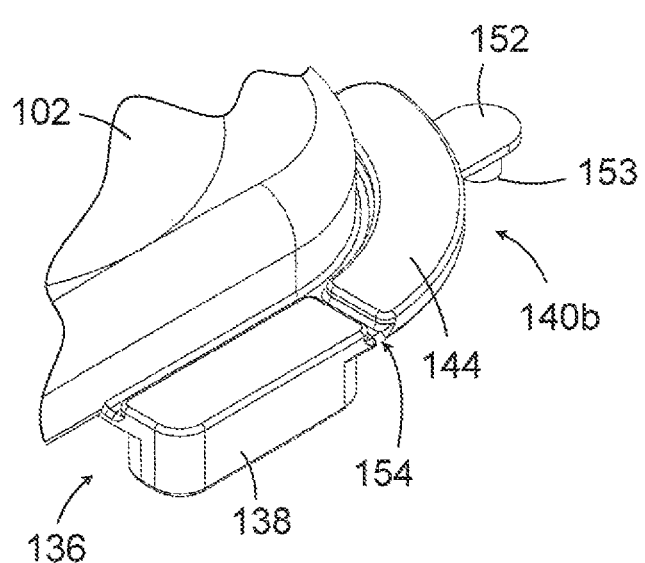
FIG. 9B is a top perspective view of a portion of a cochlear implant in accordance with one embodiment of a present invention.
Figure 9C:
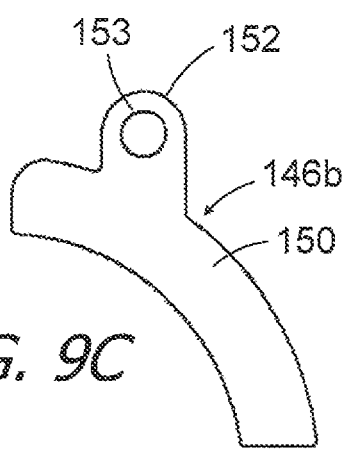
FIG. 9C is a plan view of a portion of the cochlear implant illustrated in FIG. 9B.
Figure 9D:
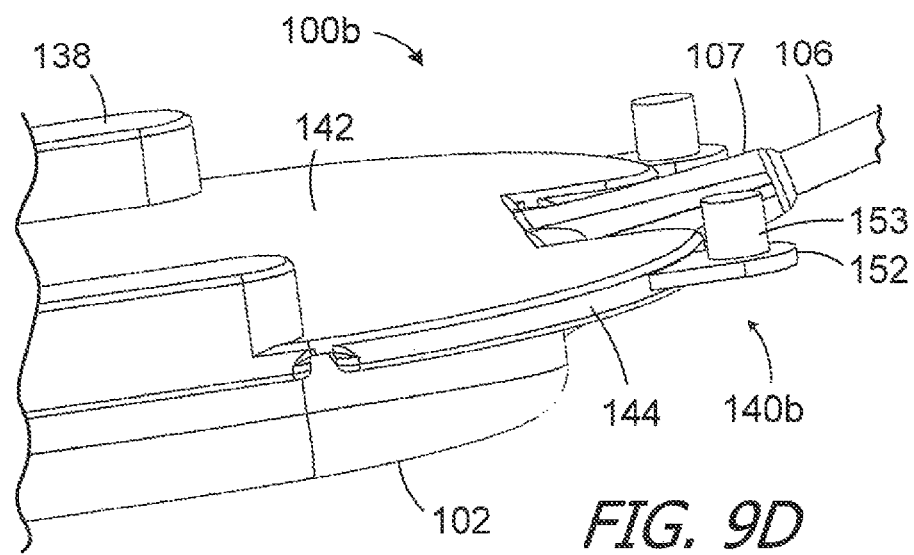
FIG. 9D is a bottom perspective view of a portion of the cochlear implant illustrated in FIG. 9B.

Another exemplary cochlear implant is represented by reference numeral 100b in FIGS. 9B-9D. The cochlear implant 100b is substantially similar to cochlear implant 100 and similar elements are represented by similar reference numerals. Here, however, the anchor receivers 140 (FIGS. 3 and 6) have been replaced by a pair of osseointegration assemblies 140b. The exemplary osseointegration assemblies 140b each include a base 144 and a lug 146b. The lug 146 has an embedded portion 150 located within the associated base 144, a tab 152 that extends outwardly from the base, and an osseointegration protrusion 153 that extends downwardly from the tab. The bone adjacent to the osseointegration protrusions 153 will over time form a bond with the protrusions, thereby fixing the position of the cochlear implant 100b.

Figure 9E:
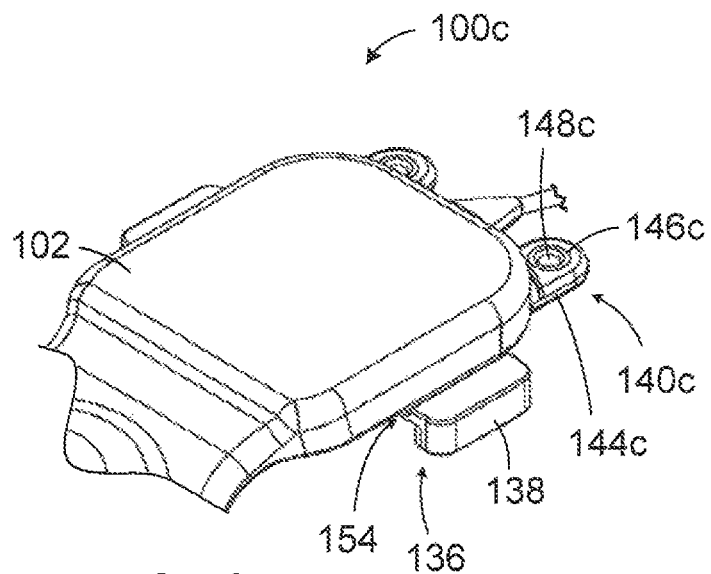
FIG. 9E is a top perspective view of a portion of a cochlear implant in accordance with one embodiment of a present invention.
Figure 9F:
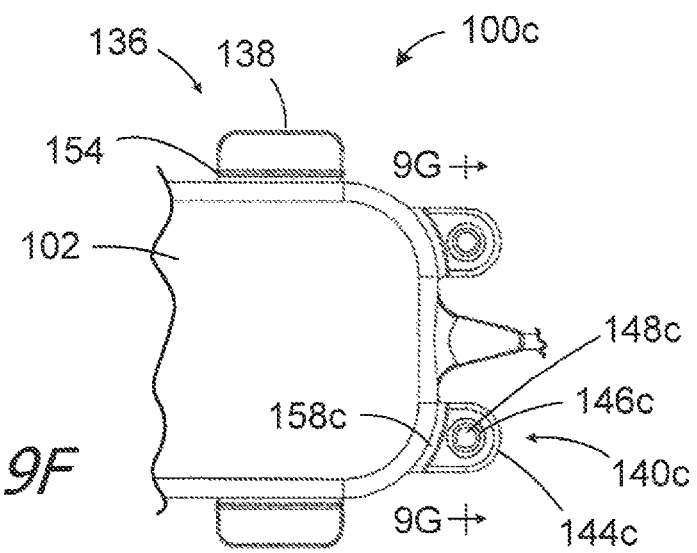
FIG. 9F is a plan view of a portion of the cochlear implant illustrated in FIG. 9E.
Figure 9G:
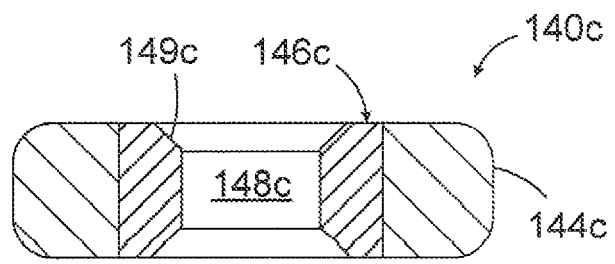
FIG. 9G is a section view taken along line 9G-9G in FIG. 9F.

Still another exemplary cochlear implant is represented by reference numeral 100c in FIGS. 9E-9G. The cochlear implant 100c is substantially similar to cochlear implant 100 and similar elements are represented by similar reference numerals. Here, however, the anchor receivers 140c include a tab-like base 144c and a grommet 146c, with an aperture 148c, that is embedded in the tab-like base. Bone screws (e.g., standard bone screws and self-drilling bone screws) or other suitable anchors may be inserted through the apertures 148c in the grommets 146c to secure the anchor receivers 140c to bone, thereby fixing the position of the cochlear implant 100c. To that end, the grommets 146c may include beveled guide surfaces 149c (FIG. 9G) for the anchors. Suitable materials for the grommets 146c include, but are not limited to, metals such as titanium and stainless steel, biocompatible polymers such as PEEK and liquid crystal polymer. With respect to potential removal of the anchor receivers 140c, thin connectors 158c are used to connect the anchor receivers 140c to the housing 102.

Figure 10:
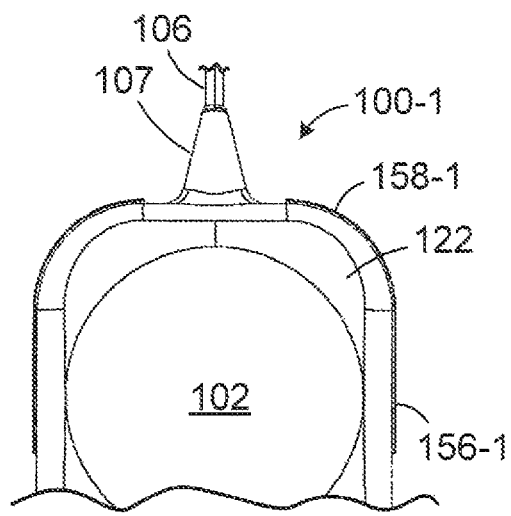
FIG. 10 is a plan view of a portion of the cochlear implant illustrated in FIG. 1 with all of the fixation elements detached.

In those instances where the surgeon prefers to rely on the formation of a tight periosteum pocket and/or anchor sutures that extend over the cochlear implant to fix the position of the implant, both the bone bed projections 138 and the anchor receivers 140 (as well as the other bone bed projections and anchor receivers described herein) may be detached and removed from the exemplary cochlear implant 100 (FIGS. 1-9), which results in the illustrated modified cochlear implant 100-1 illustrated in FIG. 10. Depending upon the manner in which the bone bed projections 138 and the anchor receivers 140 are detached from the housing 102, the modified cochlear implant 100-1 may include connector portion remainders 156-1 and 158-1.

Figure 11:
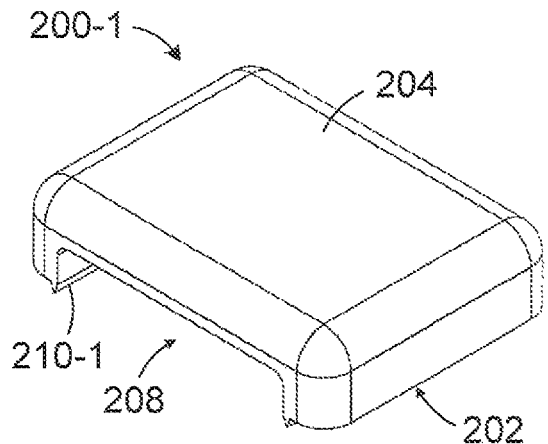
FIG. 11 is a top perspective view of a tool in accordance with one embodiment of a present invention.
Figure 12:
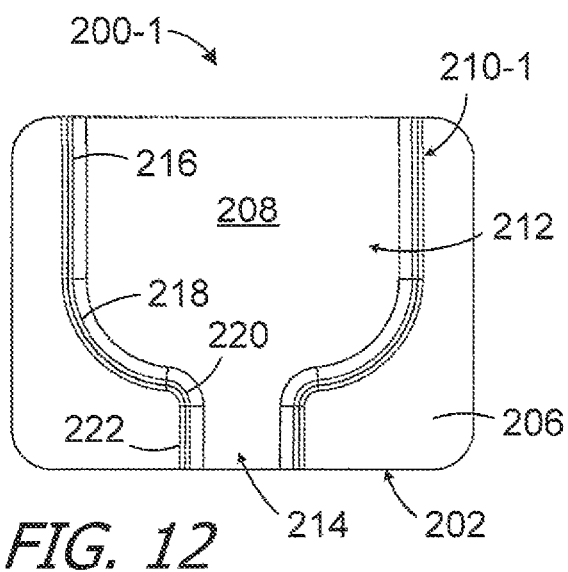
FIG. 12 is a bottom view of the tool illustrated in FIG. 11.
Figure 13:
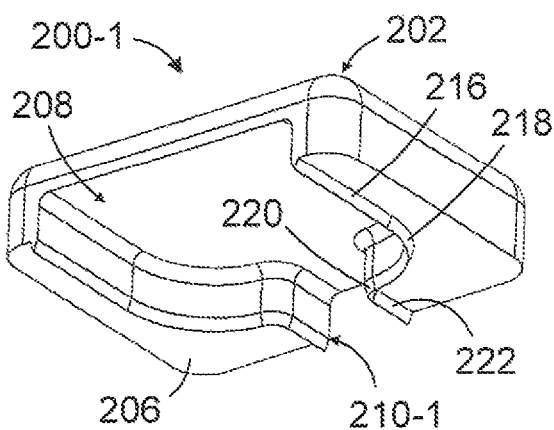
FIG. 13 is a bottom perspective view of the tool illustrated in FIG. 11.

One example of a tool which may be used to detach both the bone bed projections 138 and anchor receivers 140 is the detachment tool (or "tool") 200-1 illustrated in FIGS. 11-13. The tool 200-1, which may be used in the manner illustrated in FIGS. 14-16, includes a main body 202 with top and bottom surfaces 204 and 206, an indentation 208 that is associated with the bottom surface, and a pair of blades 210-1. The indentation 208 has a first portion 212 with a size and shape corresponding to the size and shape of the processor portion 122 of the cochlear implant housing 102, and a second portion 214 for accommodating the cochlear lead 106 and strain relief 107. The blades 210-1, which are configured to cut and sever the connector portions 156 and 158, follow the inner edges of the indentation 208 and extend downwardly from the bottom surface 206. Each blade 210-1 has a straight portion 216, curved portions 218 and 220, and a straight portion 222. During use, the blade straight portions 216 sever the connector portions 156 and the blade curved portions 218 sever the connector portions 158.

The tool 200-1 (as well as the tools 200-2 and 200-3 discussed below) may be formed from any suitable material. By way of example, but not limitation, the tools 200-1 to 200-3 may be formed entirely from metal, such as 316 stainless steel, and their blades 210-1 to 210-3 may be flame hardened. In other implementations, the main body 202 may be formed from hard plastic and metal blades may be molded into the hard plastic. In still other implementations, the tools 200-1 to 200-3 may be formed entirely from hard plastic.

Figure 14:
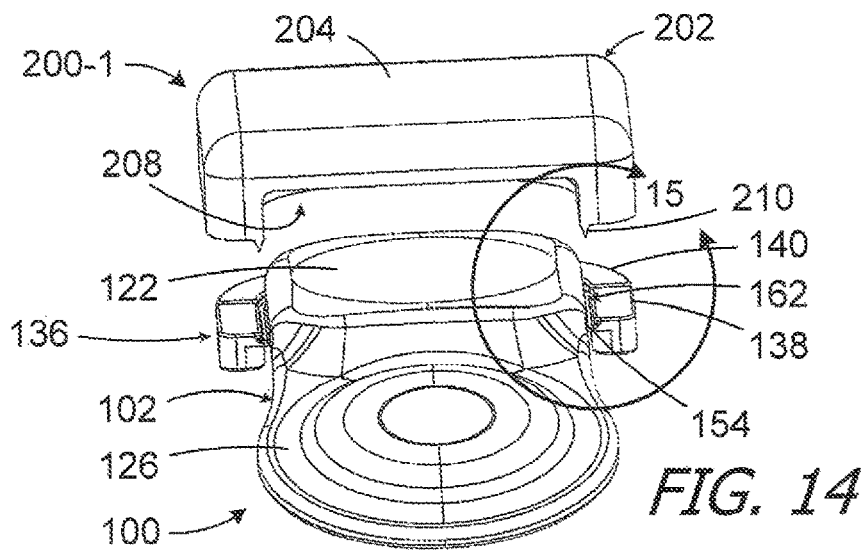
FIG. 14 is a perspective view showing a portion of a method in accordance with one embodiment of a present invention.
Figure 15:
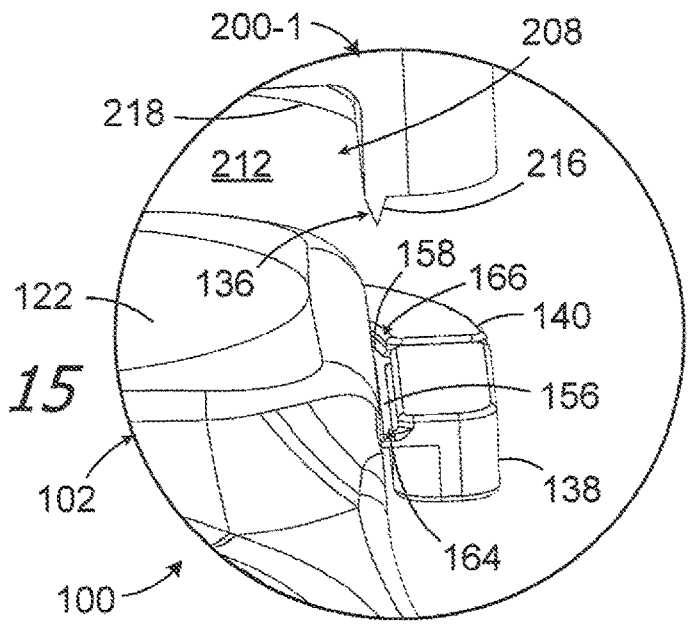
FIG. 15 is an enlarged view of a portion of FIG. 14.
Figure 16:
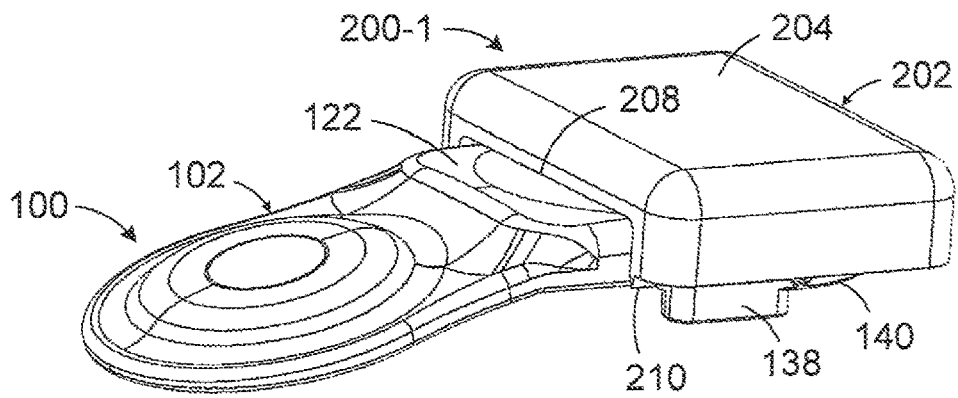
FIG. 16 is a perspective view showing a portion of a method in accordance with one embodiment of a present invention.

The manner in which the tool 200-1 may be used to detach the bone bed projections 138 and anchor receivers 140 from the cochlear implant 100 is illustrated in FIGS. 14-16. The tool 200-1 may be initially positioned in spaced relation to the cochlear implant 100 in the manner illustrated in FIGS. 14 and 15. Here, the first portion 212 of the indentation 208 is aligned with the processor portion 122 of the housing 102, and the blades 210-1 are aligned with the connectors 154 and the indentations 162. In particular, straight portions 216 of the blades 210-1 will be aligned with indentation portions 164, which will guide the blade straight portions 216 into contact with the connector portions 156, and the curved portions 218 of the blades 210-1 will be aligned with indentation portions 166, which will guide the blade curved portions 218 into contact with the connector portions 158. The cochlear implant 100 and the tool 200-1 may then be pressed against one another in the manner illustrated in FIG. 16. The respective configurations of the cochlear implant 100 and the tool 200-1, such as the thickness of the cochlear implant housing 102, the depth of the indentation 108 and the distance that the blades 210-1 extend from the bottom surface 206 of the tool, result in the blades passing through (and severing) the connector portions 156 and 158, thereby detaching the bone bed projections 138 and anchor receivers 140 from the cochlear implant 100.

Figure 17:
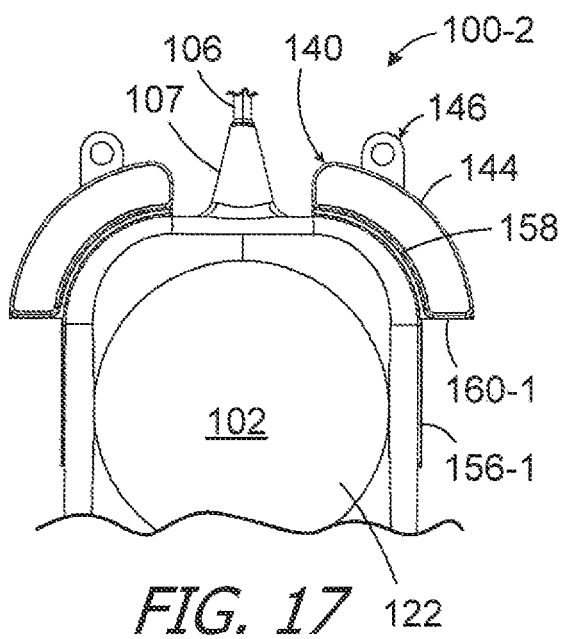
FIG. 17 is a plan view of a portion of the cochlear implant illustrated in FIG. 1 with some of the fixation elements detached.

In those instances where the surgeon prefers to rely on bone anchors to fix the position of the implant, the bone bed projections 138 may be removed from the exemplary cochlear implant 100 (FIGS. 1-9), which results in the modified cochlear implant 100-2 illustrated in FIG. 17.

Depending upon the manner in which the bone bed projections 138 are detached from the housing 102, the modified cochlear implant 100-2 may include connector portion remainders 156-1 and 160-1.

Figure 18:
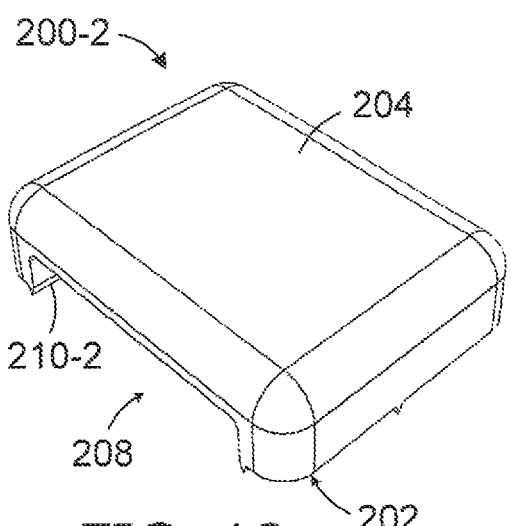
FIG. 18 is a top perspective view of a tool in accordance with one embodiment of a present invention.
Figure 19:
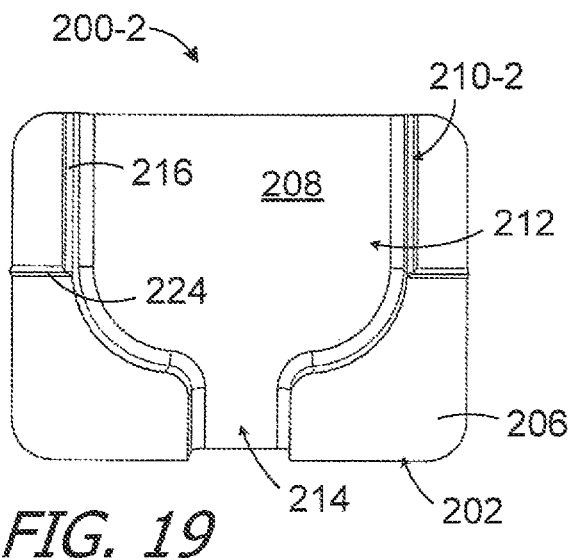
FIG. 19 is a bottom view of the tool illustrated in FIG. 18.
Figure 20:
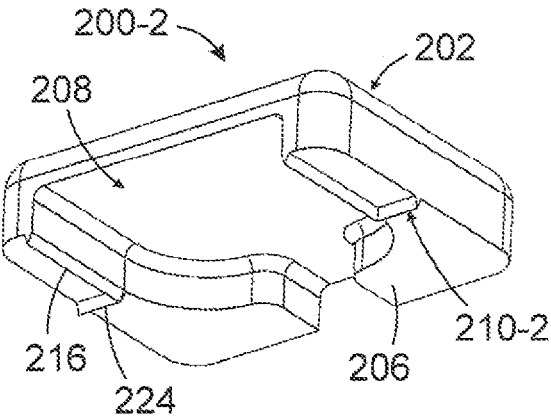
FIG. 20 is a bottom perspective view of the tool illustrated in FIG. 18.

One example of a tool which may be used to detach the bone bed projections 138 without detaching the anchor receivers 140 is the tool 200-2 illustrated in FIGS. 18-20. The tool 200-2, which may be used in the manner discussed above with reference FIGS. 14-16, is substantially similar to the tool 200-1 and similar elements are represented by similar reference numerals. For example, the tool 200-2 includes a main body 202 with top and bottom surfaces 204 and 206, and an indentation 208 that has a first portion 212 with a size and shape corresponding to the size and shape of the processor portion 122 of the housing 102 and a second portion 214 for accommodating the cochlear lead 106 and strain relief 107. Here, however, the blades 210-2 are configured to sever the connector portions 156 and 160 and, to that end, each blade 210-2 has a straight portion 216 and a straight portion 224 that is perpendicular to the straight portion 216. When used in the manner described above with reference to FIGS. 14-16, the blade straight portions 216 and 224 will pass through (and sever) the connector portions 156 and 160, thereby detaching the bone bed projections 138 from the cochlear implant 100 without detaching the anchor receivers 140.

Figure 21:
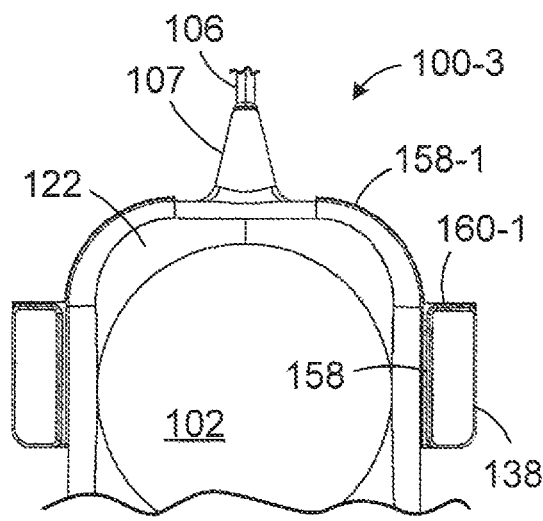
FIG. 21 is a plan view of a portion of the cochlear implant illustrated in FIG. 1 with some of the fixation elements detached.

In those instances where the surgeon prefers to rely on the bone bed projections 138 to fix the position of the implant, the anchor receivers 140 may be removed from the exemplary cochlear implant 100 (FIGS. 1-9), which results in the modified cochlear implant 100-3 illustrated in FIG. 21. Depending upon the manner in which the anchor receivers 140 are detached from the housing 102, the modified cochlear implant 100-3 may include connector portion remainders 158-1 and 160-1.

Figure 22:
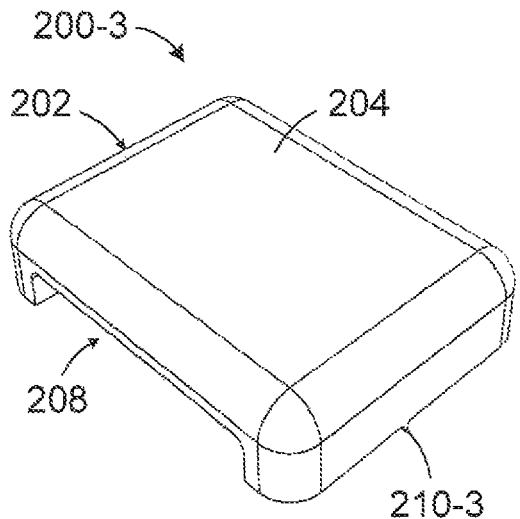
FIG. 22 is a top perspective view of a tool in accordance with one embodiment of a present invention.
Figure 23:
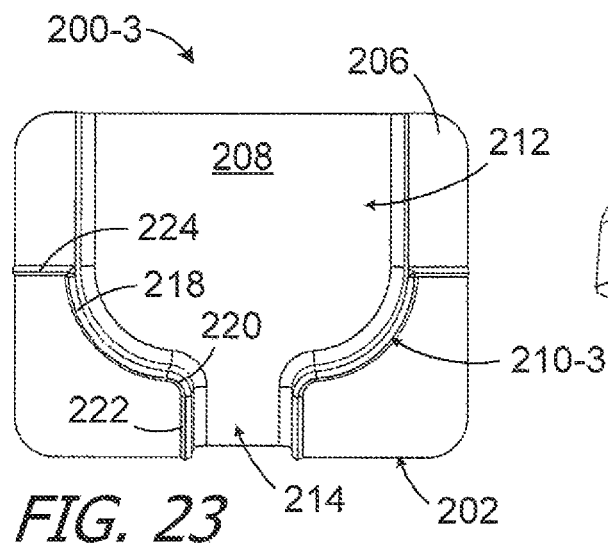
FIG. 23 is a bottom view of the tool illustrated in FIG. 22.
Figure 24:
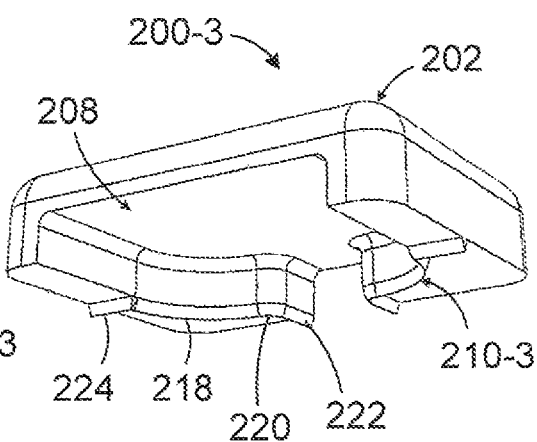
FIG. 24 is a bottom perspective view of the tool illustrated in FIG. 22.

One example of a tool which may be used to detach the anchor receivers 140 without detaching the bone bed projections 138 is the tool 200-3 illustrated in FIGS. 22-24. The tool 200-3, which may be used in the manner discussed above with reference FIGS. 14-16, is substantially similar to the tool 200-1 and similar elements are represented by similar reference numerals. For example, the tool 200-3 includes a main body 202 with top and bottom surfaces 204 and 206, and an indentation 208 that has a first portion 212 with a size and shape corresponding to the size and shape of the processor portion 122 of the housing 102 and a second portion 214 for accommodating the cochlear lead 106 and strain relief 107. Here, however, the blades 210-3 are configured to sever the connector portions 158 and 160 and, to that end, each blade 210-3 has curved portions 218 and 220 and straight portions 222 and 224. When used in the manner described above with reference to FIGS. 14-16, the blade curved and straight portions 218 and 224 will pass through (and sever) the connector portions 158 and 160, thereby detaching the anchor receivers 140 from the cochlear implant 100 without detaching the bone bed projections 138.

Figure 25:
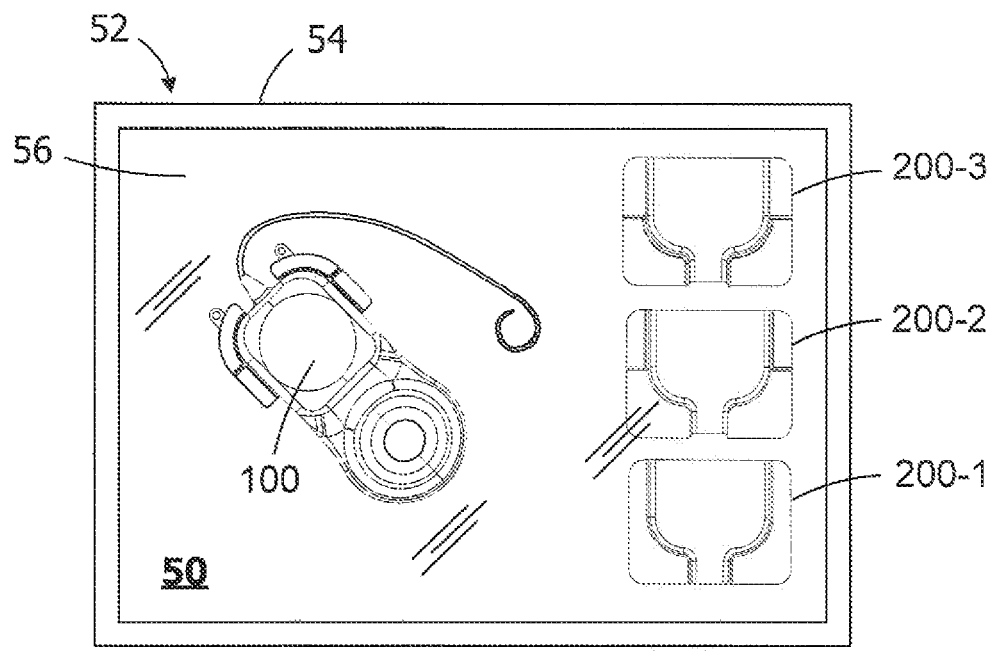
FIG. 25 is a plan view of a cochlear implant kit in accordance with one embodiment of a present invention.

One example of a system (or "kit") 50 in accordance with at least one of the present inventions includes the exemplary cochlear implant 100 (or cochlear implant 100a or 100b or 100c) as well as the exemplary tools 200-1, 200-2 and 200-3. As illustrated for example in FIG. 25, the cochlear implant 100 and tools 200-1, 200-2 and 200-3 may be housed in a sterile package 52 that has a flat rigid bottom portion 54 and a top transparent top cover 56, thereby providing a ready to use surgical kit. The bottom portion 54 may be formed from a material which allows the contents of the package to be sterilized after being sealed within the package. The present kit 50 can be provided to all surgeons, with both the package and contents in a sterile state, because the contents of the kit will accommodate whichever fixation technique the surgeon prefers. The kit 50 may also be a single-use kit, i.e., the tools and detached fixation elements may be discarded after the cochlear implant has been implanted.

Figure 26:
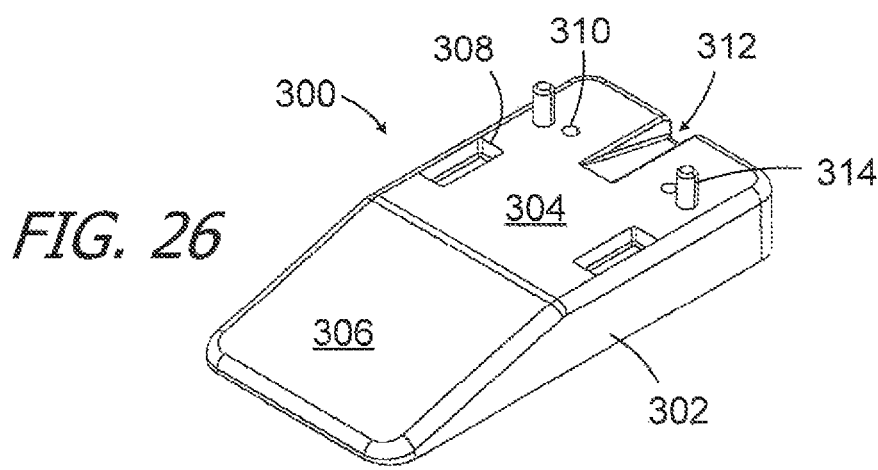
FIG. 26 is a top perspective view of a fixture in accordance with one embodiment of a present invention.
Figure 27:
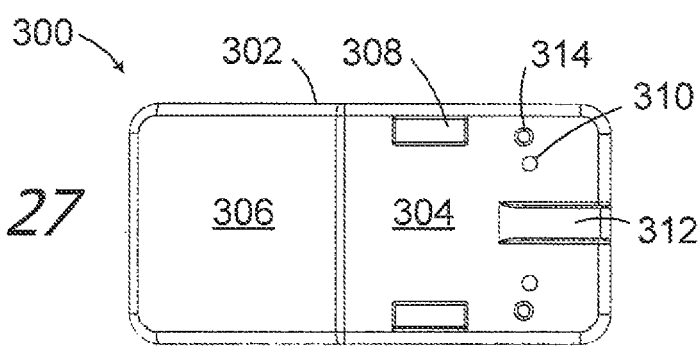
FIG. 27 is a top view of the fixture illustrated in FIG. 26.

There may also be some surgeons who prefer to use a fixture that is configured to support the cochlear implant and properly align the detachment tool with the cochlear implant. One example of such a detachment fixture is generally represented by reference numeral 300 in FIGS. 26 and 27. The exemplary fixture 300 includes a main body 302 with top surfaces 304 and 306 that support respective portions of the associated cochlear implant in the manner described below with reference to FIGS. 30-32. Apertures 308 and 310 extend into the main body 302 from the top surface 304, as does a recess 312. The apertures 308 accommodate the bone bed projections 138, while the anchor receivers 140 simply rest on the top surface 304. In the illustrated implementation, the top surfaces 304 and 306 together define a non-zero angle that corresponds to the relaxed shape of the associated cochlear implant. The length and width of the illustrated apertures 308 may correspond to that of the bone bed projections 138 in order to ensure that cochlear implant 100 (or 100b or 100c) is in the intended location. The configuration of the apertures 308 may be adjusted, if necessary, to accommodate the cantilevered flap 141 of cochlear implant 100a. The apertures 310 accommodate the osseointegration protrusions 153 in those instances where they are present. The strain relief 107 and end of the cochlear lead 106 will be located in the recess 312. Alignment posts 314 extend upwardly from the main body 302, and will guide the detachment tool as it moves toward the cochlear implant in the manner described below. Suitable materials for the fixture 300 include, but are not limited to, plastic such as PEEK and nylon.

Figure 28:
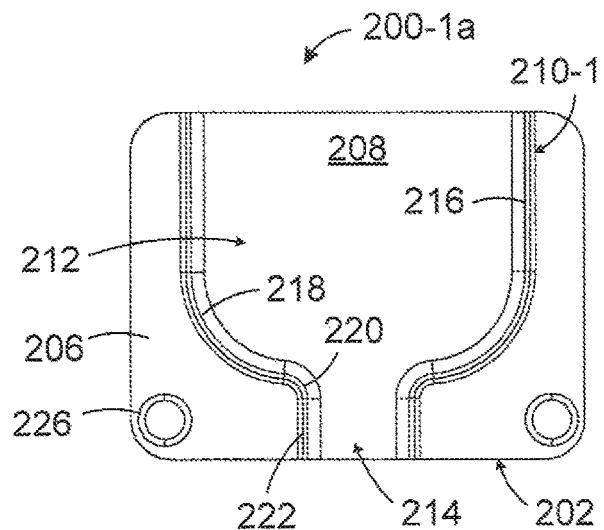
FIG. 28 is a bottom view of a tool in accordance with one embodiment of a present invention.

The exemplary detachment fixture 300 may be used in conjunction with, for example, modified versions of the detachment tools 200-1 to 200-3 described above. To that end, and referring to FIG. 28, the exemplary detachment tool 200-1a is identical to the 200-1 but for the addition of a pair of alignment post receptacles 226 that extend into the main body 202 by way of the bottom surface 206. The cross-sectional size and shape of the alignment post receptacles 226, as well as the distance between the receptacles, corresponds to that of the alignment posts 314. In addition, the respective positions of the cochlear implant bone bed apertures 138 and connectors 154, the blades 210-1 and alignment post receptacles 226 of the tool 200-1a, and the bone projection apertures 308 and alignment posts 314 of the fixture 300 result in the blades 210-1 being aligned with the connectors 154 (FIG. 6) when the alignment posts 314 are located within the receptacles 226. Additionally, the length of the blades 210-1 (measured perpendicular to bottom surface 206) is such that the blades will sever the appropriate portions of the connector 154 when (or prior to) the bottom surface 206 reaches the cochlear implant fixation apparatus 136.

It should be noted here that the discussion above concerning tool 200-1a is equally applicable to tool 200-2a (FIG. 33), which is identical to tool 200-2 but for the alignment post receptacles 226, and tool 200-3a (FIG. 33), which is identical to tool 200-3 but for the alignment post receptacles 226. Additionally, in some implementations, the locations of the alignment posts 314 and alignment post receptacles 226 may be reversed, i.e., the posts may be located on the tools and the receptacles may be located on the fixture. The cross-sectional shapes of the alignment posts and alignment post receptacles are not limited to the illustrated circular shape. Other shapes, including but not limited to square, oval and hexagonal, may be employed.

Figure 29:
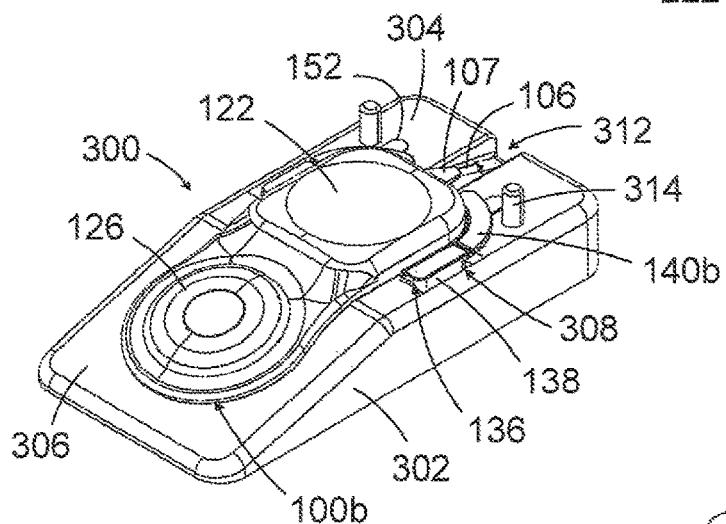
FIG. 29 is a top perspective view showing a portion of a method in accordance with one embodiment of a present invention.

The detachment tool 200-1a and fixture 300 may be used in the exemplary manner illustrated in FIGS. 29-32 to detach fixation elements from a cochlear implant (e.g., cochlear implant 100, 100a or 100b). Referring first to FIG. 29, a cochlear implant such as cochlear implant 100b may be placed onto the fixture 300 in such a manner that the bone bed projections 138 are located within the apertures 308 and the osseointegration protrusions 153 are located within the apertures 310. Here, the processor portion 122 of the cochlear implant housing 102 is located on the top surface 304, the antenna portion 126 is located on the top surface 306, and the strain relief 107 and end of the cochlear lead 106 are located in the recess 312.

Figure 30:
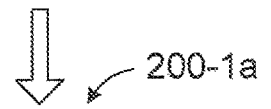
FIG. 30 is a side view showing a portion of a method in accordance with one embodiment of a present invention.
Figure 30:
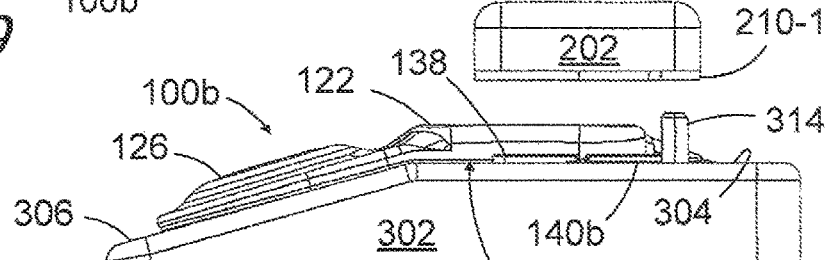
Figure 31:
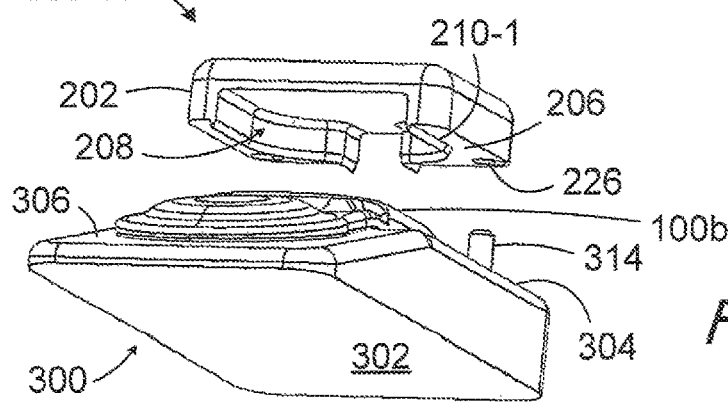
FIG. 31 is a bottom perspective view showing a portion of a method in accordance with one embodiment of a present invention.
Figure 32:
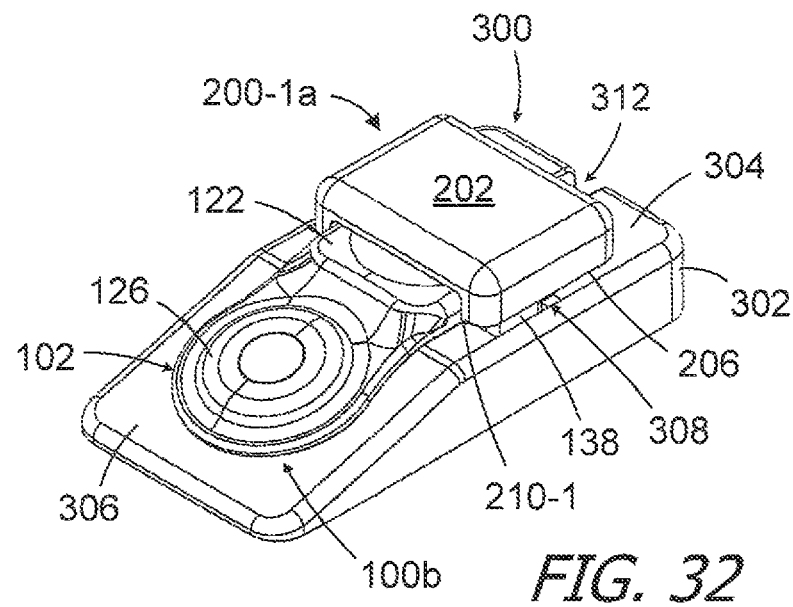
FIG. 32 is a top perspective view showing a portion of a method in accordance with one embodiment of a present invention.

Next, as shown in FIGS. 30 and 31, the tool 200-1a may be positioned over the cochlear implant 100b and fixture 300 in such a manner that the alignment post receptacles 226 are in-line (i.e., are coaxial) with alignment posts 314. The tool 200-1a may then be moved toward the fixture 300 in such a manner that the alignment posts 314 enter the post receptacles 226. Such movement may continue until the blades 210-1a sever the appropriate connector portions, i.e., connector portions 156 and 158 in the illustrated example, to produce a modified cochlear implant, i.e., modified cochlear implant 100-1 (FIG. 10) in the illustrated example.

Figure 33:
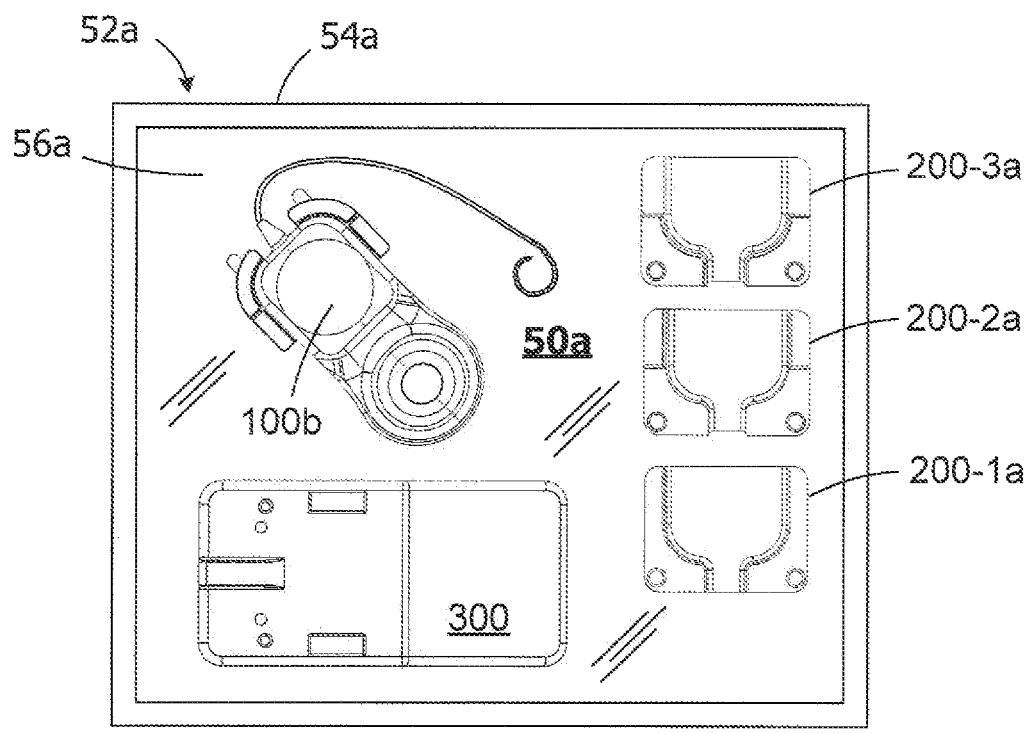
FIG. 33 is a plan view of a cochlear implant kit in accordance with one embodiment of a present invention.

Another exemplary system (or "kit") is generally represented by reference numeral 50a in FIG. 33. Kit 50a is includes the exemplary cochlear implant 100b (or cochlear implant 100 or 100a), the exemplary tools 200-1a, 200-2a and 200-3a, and the fixture 300. The cochlear implant 100b, tools 200-1a, 200-2a and 200-3a, and fixture 300 may be housed in a sterile package 52a that has a flat rigid bottom portion 54a and a top transparent top cover 56a, thereby providing a ready to use surgical kit. The bottom portion 54a may be formed from a material which allows the contents of the package to be sterilized after being sealed within the package. The present kit 50a can be provided to all surgeons, with both the package and contents in a sterile state, because the contents of the kit will accommodate whichever fixation technique the surgeon prefers. The kit 50a may also be a single-use kit, i.e., the tools and detached fixation elements may be discarded after the cochlear implant has been implanted.

Figure 34:
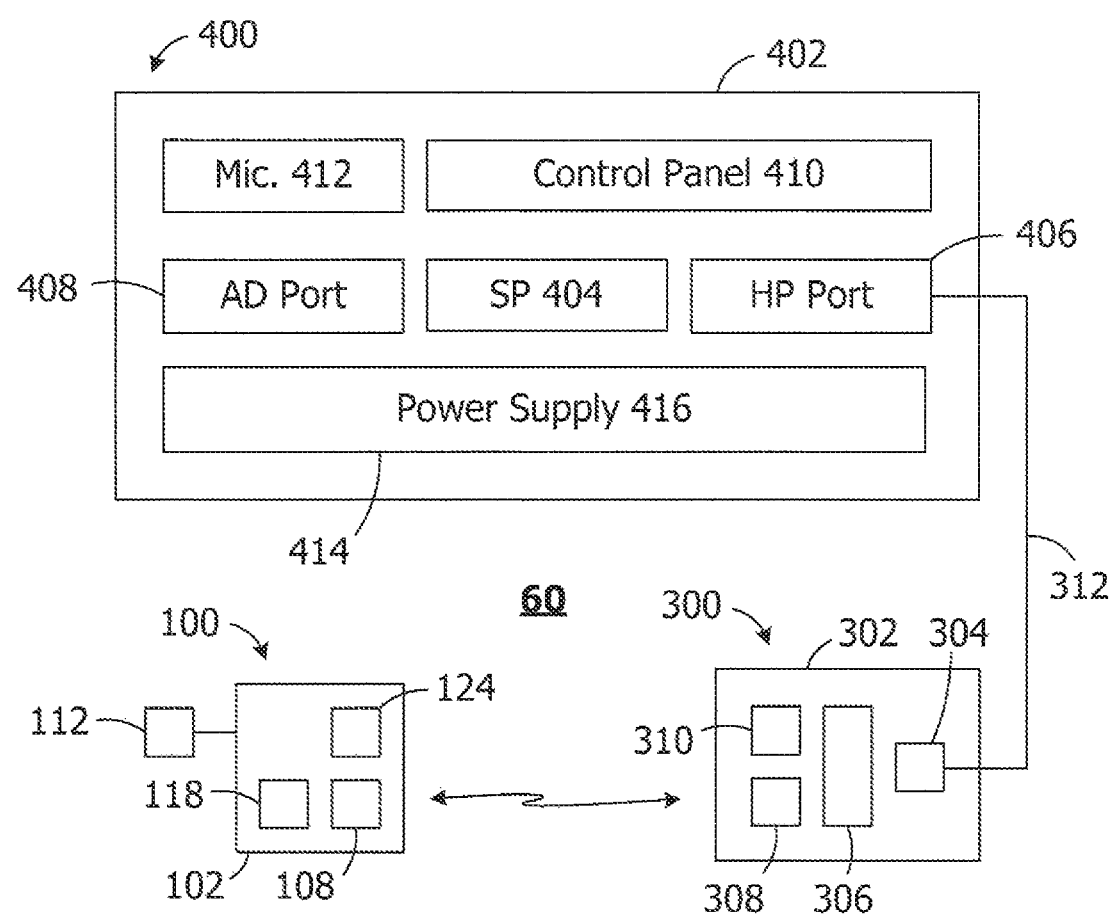
FIG. 34 is a block diagram of a cochlear implant system in accordance with one embodiment of a present invention.

As illustrated in FIG. 34, the exemplary cochlear implant system 60 includes the cochlear implant 100 (or 100a or 100b or 100c), a sound processor, such as the illustrated body worn sound processor 400 or a behind-the-ear sound processor, and a headpiece 300.

The exemplary body worn sound processor 400 in the exemplary ICS system 60 includes a housing 402 in which and/or on which various components are supported. Such components may include, but are not limited to, sound processor circuitry 404, a headpiece port 406, an auxiliary device port 408 for an auxiliary device such as a mobile phone or a music player, a control panel 410, one or microphones 412, and a power supply receptacle 414 for a removable battery or other removable power supply 416 (e.g., rechargeable and disposable batteries or other electrochemical cells). The sound processor circuitry 404 converts electrical signals from the microphone 412 into stimulation data. The exemplary headpiece 300 includes a housing 302 and various components, e.g., a RF connector 304, a microphone 306, an antenna (or other transmitter) 308 and a positioning magnet apparatus 310, that are carried by the housing. The magnet apparatus 310 may consist of a single magnet or may consist of one or more magnets and a shim. The headpiece 300 may be connected to the sound processor headpiece port 406 by a cable 312. The positioning magnet apparatus 310 is attracted to the magnet 124 of the cochlear stimulator 100, thereby aligning the antenna 308 with the antenna 108. The stimulation data and, in many instances power, is supplied to the headpiece 300. The headpiece 300 transcutaneously transmits the stimulation data, and in many instances power, to the cochlear implant 100 by way of a wireless link between the antennas. The stimulation processor 118 converts the stimulation data into stimulation signals that stimulate the contacts 114 of the electrode array 112.

In at least some implementations, the cable 312 will be configured for forward telemetry and power signals at 49 MHz and back telemetry signals at 10.7 MHz. It should be noted that, in other implementations, communication between a sound processor and a headpiece and/or auxiliary device may be accomplished through wireless communication techniques. Additionally, given the presence of the microphone(s) 412 on the sound processor 400, the microphone 306 may be also be omitted in some instances. The functionality of the sound processor 400 and headpiece 300 may also be combined into a single head wearable sound processor. Examples of head wearable sound processors are illustrated and described in U.S. Pat. Nos. 8,811,643 and 8,983,102, which are incorporated herein by reference in their entirety.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A cochlear implant kit, comprising
a cochlear implant including
    a cochlear lead including an electrode array,
    a housing,
    an antenna within the housing,
    a stimulation processor within the housing operably connected to the antenna and to the cochlear lead,
    a first fixation element attached to the housing, and
    a second fixation element attached to the housing, the second fixation element being a different type of fixation element than the first fixation element;
a first tool including a main body, with an indentation having a shape corresponding to at least a portion of the cochlear implant housing, and a first blade that is adjacent to the indentation and is configured to detach at least the first fixation element from the housing, without detaching the second fixation element, when the first tool is pressed against the portion of the cochlear implant housing; and
a second tool including a main body, with an indentation having a shape corresponding to at least the portion of the cochlear implant housing, and a second blade that is adjacent to the indentation and is configured to detach at least the second fixation element from the housing, without detaching the first fixation element, when the second tool is pressed against the portion of the cochlear implant housing.

2. A cochlear implant kit as claimed in claim 1, wherein
the first fixation element comprises a pair of first fixation elements; and
the second fixation element comprises a pair of second fixation elements.

3. A cochlear implant kit as claimed in claim 1, further comprising:
first and second connector portions that connect the first and second fixation elements to the housing; wherein
the first blade is configured to sever the first connector portion when the first tool is pressed against the portion of the cochlear implant housing; and
the second blade is configured to sever the second connector portion when the second tool is pressed against the portion of the cochlear implant housing.

4. A cochlear implant kit as claimed in claim 1, further comprising:
a third tool configured to detach both of the first and second fixation elements from the housing when the third tool is pressed against the portion of the cochlear implant housing.

5. A cochlear implant kit as claimed in claim 1, further comprising:
a fixture configured to align the first and second tools with cochlear implant.

6. A cochlear implant kit as claimed in claim 5, wherein
one of the fixture and one of the first and second tools includes one or more alignment post receptacles, and the other of the fixture and one of the first and second tools includes one or more alignment posts.

7. A cochlear implant kit as claimed in claim 1, further comprising:
a sterile package in which the cochlear implant and the first and second tools are located.

8. A cochlear implant kit as claimed in claim 1, wherein
the first fixation element comprises a bone bed projection; and
the second fixation element is selected from the group consisting of an anchor receiver and an osseointegration assembly.

9. A method of implanting a cochlear implant that includes a housing, a plurality of first fixation elements connected to the housing and a plurality of second fixation elements connected to the housing, the second fixation elements having a different configuration than the first fixation elements, the method comprising the steps of:
simultaneously detaching the first fixation elements from the cochlear implant by cutting through portions of the cochlear implant; and
implanting the cochlear implant into a patient after the first fixation elements have been detached.

10. A method as claimed in claim 9, wherein
simultaneously detaching the first fixation elements comprises simultaneously detaching the first fixation elements without detaching the second fixation elements.

11. A method as claimed in claim 9, further comprising:
detaching the second fixation elements simultaneously with the first fixation elements.

12. A cochlear implant kit, comprising
a cochlear implant including
a cochlear lead including an electrode array,
a housing,
an antenna within the housing,
a stimulation processor within the housing operably connected to the antenna and to the cochlear lead,
a first fixation element having a non-zero thickness and a shape;
a first connector portion having a non-zero thickness that is less than the thickness of the first fixation element, wherein the first connector portion attaches the first fixation element to the housing,
a second fixation element located adjacent to the first fixation element and having a non-zero thickness and a shape that are different than the non-zero thickness and the shape of the first fixation element, and
a second connector portion having a non-zero thickness that is less than the thickness of the second fixation element, wherein the second connector portion attaches the second fixation element to the housing;
a first tool configured to detach at least the first fixation element from the housing when the cochlear implant and the first tool are pressed against one another; and
a second tool configured to detach at least the second fixation element from the housing when the cochlear implant and the second tool are pressed against one another.

13. A cochlear implant kit as claimed in claim 12, wherein
the first fixation element comprises a pair of first fixation elements; and
the second fixation element comprises a pair of second fixation elements.

14. A cochlear implant kit as claimed in claim 12, wherein
the first tool is configured to detach the first fixation element from the housing without detaching the second fixation element from the housing when the cochlear implant and the first tool are pressed against one another; and
the second tool is configured to detach the second fixation element from the housing without detaching the first fixation element from the housing when the cochlear implant and the second tool are pressed against one another.

* * * * *